(12) United States Patent
Cavazza

(10) Patent No.: US 7,585,896 B2
(45) Date of Patent: Sep. 8, 2009

(54) COMPOSITION FOR THE PREVENTION AND TREATMENT OF KIDNEY DYSFUNCTIONS AND DISEASES

(75) Inventor: Claudio Cavazza, Rome (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 561 days.

(21) Appl. No.: 10/667,482

(22) Filed: Sep. 23, 2003

(65) Prior Publication Data

US 2004/0057994 A1  Mar. 25, 2004

Related U.S. Application Data

(62) Division of application No. 10/019,545, filed as application No. PCT/IT00/00313 on Jul. 25, 2000, now Pat. No. 6,653,349.

(30) Foreign Application Priority Data

Jul. 28, 1999  (IT)  ............... RM99A0483

(51) Int. Cl.
  *A61K 31/225* (2006.01)
  *A61K 31/70* (2006.01)
(52) U.S. Cl. ........................ 514/547; 514/23
(58) Field of Classification Search ............. 514/11, 514/19, 291, 551, 556, 23, 547
  See application file for complete search history.

(56) References Cited

U.S. PATENT DOCUMENTS 5,246,835 A * 9/1993 Suzuki et al. ............... 435/7.95
5,955,424 A * 9/1999 Calvani et al. ................ 514/11
6,653,349 B1 * 11/2003 Cavazza ..................... 514/547

FOREIGN PATENT DOCUMENTS

| EP | 0 722 724 A | 7/1996 |
| WO | 98 41113 A | 9/1998 |
| WO | 98 43499 A | 10/1998 |
| WO | 99 17623 A | 4/1999 |

OTHER PUBLICATIONS

Bertelli A et al; "Proctective Effect of L-Propionylcarnitine on Cyclosporine-Induced Nephrotoxicity" Drugs Under Experimental and Clinical Research, XX, Bioscience, Ediprint Inc.; vol. 21, No. 6, 1995, pp. 221-228; XP000568312.
Kerkadi, A. et al 1998, Journal of Toxicology and Environmental Health, Part A, 53; pp. 231-250.
Galley, H.F., J. R. Coll. Surg. Edinb., 45, Feb. 2000, 44-50.

\* cited by examiner

*Primary Examiner*—Jennifer Myong M Kim
(74) *Attorney, Agent, or Firm*—Lucas & Mercanti LLP

(57) ABSTRACT

A composition is disclosed which is suitable for the prevention and treatment of kidney dysfunctions and diseases and which can therefore take the form of a food supplement or of an actual medicinal drug comprising a combination of acetyl L-carnitine and propionyl L-carnitine or their pharmacologically acceptable salts.

9 Claims, No Drawings

COMPOSITION FOR THE PREVENTION AND TREATMENT OF KIDNEY DYSFUNCTIONS AND DISEASES

This application is a divisional of application Ser. No. 10/019,545, filed Jan. 3, 2002, now U.S. Pat. No. 6,653,349, which in turn is a 35 U.S.C. 371 of PCT/IT00/00313 filed Jul. 25, 2000.

The present invention relates to a composition suitable for the prevention and treatment of kidney dysfunctions and diseases.

Correspondingly, the composition may take the form and exert the activity of a food supplement or of an actual medicinal drug, depending upon the support or preventive action or the strictly therapeutic action which the composition is intended to exert according to the particular individuals for whom it is to be used.

More specifically, the composition according to the present invention is suitable for the prevention and treatment of all forms of nephropathy, whether caused by external agents such as nephrotoxic drugs like lithium, antibiotics and anticancer drugs with a nephrotoxic potential, environmental contaminants such as mycotoxins of the ochratoxin type, or due to kidney function deficits of metabolic origin.

The composition according to the present invention comprises as its characterising ingredients acetyl L-carnitine and propionyl L-carnitine or the pharmacologically acceptable salts thereof which will be identified hereinbelow.

The use of "carnitines" in the field of nephrology (where the term "carnitines" refers collectively to both L-carnitine and to the lower alkanoyl L-carnitines such as acetyl, propionyl butyryl L-carnitine, etc.) is already known.

U.S. Pat. Nos. 4,272,549 and 4,237,167 (Sigma-Tau Industrie Farmaceutiche Riunite S.p.A) describe the use of L-carnitine and of the above-mentioned respective alkanoyl L-carnitines to prepare polysaline solutions which are fed into the dialysis compartment of artificial kidneys. The purpose of the presence of said carnitines in the dialysis fluid is to counteract the loss of L-carnitine in the blood and tissues which habitually occurs in patients undergoing regular haemodialysis treatment, with the consequent onset of disorders of the skeletal muscle and myocardium.

It is equally well known that a lack of L-carnitine may be the cause of tubular necrosis following kidney transplantation.

Finally, EP 0722 724 discloses the use of L-carnitine or lower alkanoyl L-carnitine for preparing a medicament apt to inhibit nephro- and vasculotoxicity induced by the administration of immunosuppressants such as cyclosporin-A, tacrolimus, rapamicine and deoxysparguoline; and Drugs Exptl. Clin Res. XXI (6), 221-228 (1995) specifically reports on the protective effect of propionyl L-carnitine on cyclosporine-induced nephrotoxicity.

In contrast, neither known nor suggested by the vast amount of knowledge available on the role of the carnitines and their possible therapeutic applications, particularly as developed over the past few decades, is the act that the composition according to the present invention, consisting of a combination of acetyl L-carnitine and propionyl L-carnitine or the pharmacologically acceptable salts thereof presents a potent kidney-protecting action, particularly as regards the prevention and treatment of kidney function impairments caused by toxic agents or metabolism disorders.

In the combination composition according to the invention the w/w ratio of acetyl L-carnitine to propionyl L-carnitine ranges from 1:1 to 1:10.

The composition may also contain an additional carnitine selected from the group consisting of L-carnitine, butyryl L-carnitine, valeryl L-carnitine and isovaleryl L-carnitine or their pharmacologically acceptable salts. The w/w ratio of acetyl L-carnitine and propionyl L-carnitine to this additional carnitine ranges from 1:0.5 to 1:2.

Additional optional components comprise vitamins, coenzymes, minerals and antioxidants.

It is advisable to administer 2-5 mg of acetyl L-carnitine and 2-5 mg of propionyl L-carnitine per kg body weight per day, though higher doses can also be administered in view of the very low toxicity of the components.

The marked kidney-protecting activity exerted by the combination of acetyl L-carnitine and propionyl L-carnitine is shown by the results of a number of experimental tests which are reported here below.

These tests were selected in such a way as to be predictive of the efficacy of the combination in human subjects and in the clinical field. They also demonstrate the surprisingly potent synergistic action exerted when acetyl L-carnitine and propionyl L-carnitine are used in combination.

TOXICOLOGY TESTS

Both acetyl L-carnitine and propionyl L-carnitine are known to be characterised by very low toxicity. Toxicology tests showed that even high doses of acetyl L-carnitine (750 mg/kg) in combination with propionyl L-carnitine (750 mg/kg) administered intraperitoneally to rats did not cause the deaths of any of the animals thus treated. The same result was obtained with the oral administration of 1.25 g of acetyl L-carnitine together with 1.25 g of propionyl L-carnitine.

The oral administration of 500 mg/kg of acetyl L-carnitine together with 500 mg/kg of propionyl L-carnitine for thirty consecutive days was also well tolerated.

No abnormalities of body growth or blood crasis were detected, in fact, as compared to control animals, neither were any abnormalities detected in the animals thus treated after performing blood-chemistry tests.

Anatomico-pathological and histological examinations carried out on the main organs and tissues also failed to reveal any significant abnormalities, thus confirming the very low toxicity and good tolerability of the two compounds used in combination.

Protective Activity Against Experimentally Induced Renal Insufficiency

To assess the kidney-protecting activity exerted by the combination of acetyl L-carnitine and propionyl L-carnitine, renal insufficiency resembling the so-called "crush syndrome" in man (Stein J. H., Lifschitz M. D., Bernes L. D., Am. J. Physiol: 234, F171, 1978) was experimentally induced in rats by intramuscular injection of glycerol, as described by Young (Young J. H. K., Meth. Find. Exptl. Clin. Pharmacol., 13, 23, 1991). For this purpose, different groups of anaesthetised male Sprague-Dawley rats with a mean weight of 300 g, deprived of drinking water for the previous 24 hours, received intramuscular injections of 10 mg/kg of an aqueous solution of 50% glycerol. Whereas the first of these groups was kept as a control group, the other groups were treated orally immediately after glycerol injection for the three days preceding the test with 100 mg/kg or 500 mg/kg of acetyl L-carnitine, or with 100 mg/kg or 500 mg/kg of propionyl L-carnitine or with the same doses of the two drugs in combination. Intraperitoneal administration was done for the same period of time with 50 mg/kg or 250 mg/kg of acetyl L-carnitine or with 50 mg/kg or 250 mg/kg of propionyl L-carnitine or with the same doses of the two drugs in combination. Twenty-four hours after injection, blood samples were taken from the animals thus treated as well as from the control animals. On the plasma obtained by centrifuging, creatinine was determined according to the Taussky method (Taussky H. H., Clin. Chem. Acta, 1, 20, 1956), plasma proteins according to the Lowry method (Lowry O. H., Rosembrough N. J., Fan A. L., Randall R. Y., J. Biol. Chem., 193, 265, 1951) and urea by means of reaction with diacetyl monoxime.

The glycerol-induced acute renal insufficiency was demonstrated by a substantial increase in plasma concentrations of both urea and creatinine.

Administration of acetyl L-carnitine or propionyl L-carnitine alone produced only slight changes in the elevated plasma urea and creatinine concentrations, whereas a surprisingly marked reduction was noted when acetyl L-carnitine and propionyl L-carnitine were administered in combination.

The synergistic effect of acetyl L-carnitine and propionyl L-carnitine in terms of the protection afforded against glycerol-induced renal insufficiency was marked both when acetyl L-carnitine and propionyl L-carnitine were administered orally and when they were administered intraperitoneally (see Table 1).

TABLE 1

Protective activity against glycerol-induced renal insufficiency

| Treatm. | mg/kg | Admin. route | Urea (mg/100 ml) | Creatinine (mg/100 ml) | Proteins (mg/100 ml) |
|---|---|---|---|---|---|
| Controls | | | 20.5 ± 2.1 | 55.8 ± 9.9 | 62.6 ± 5.9 |
| Glycerol | | | 120.5 ± 27.5 | 360.7 ± 25.5 | 66.2 ± 7.2 |
| ACL | 100 | oral | 110.9 ± 21.6 | 320.4 ± 20.6 | 65.2 ± 6.9 |
| ACL | 500 | " | 105.4 ± 29.4 | 315.9 ± 35.5 | 65.3 ± 7.2 |
| PC | 100 | " | 107.4 ± 30.2 | 295.1 ± 28.4 | 65.9 ± 8.1 |
| PC | 500 | " | 90.2 ± 31.4 | 280.8 ± 30.2 | 64.1 ± 9.4 |
| ACL + PC | 100 100 | " | 72.6 ± 12.4 | 165.2 ± 20.4 | 63.1 ± 6.5 |
| ACL + PC | 500 500 | " | 39.7 ± 15.6 | 80.4 ± 14.8 | 62.7 ± 6.1 |
| ACL | 100 | i.p. | 104.7 ± 12.4 | 300.5 ± 30.1 | 65.2 ± 6.6 |
| ACL | 500 | " | 98.5 ± 10.6 | 280.4 ± 21.7 | 64.4 ± 5.5 |
| PC | 100 | " | 100.5 ± 9.8 | 270.9 ± 29.4 | 62.4 ± 7.1 |
| PC | 500 | " | 80.2 ± 6.6 | 260.6 ± 20.9 | 63.6 ± 7.5 |
| ACL + PC | 100 100 | " | 55.9 ± 11.5 | 155.1 ± 18.4 | 63.3 ± 5.9 |
| ACL + PC | 500 500 | " | 35.5 ± 5.9 | 75.2 ± 6.2 | 62.9 ± 6.3 |

ACL = Acetyl L-carnitine
PC = Propionyl L-carnitine

Protective Activity Against Experimentally Induced Renal Toxic Lesions

In experimental animals, particularly rats, it is possible to reproduce tubulo-interstitial nephropathy similar to that encountered in man and known as Balkans Endemic Nephropathy (BEN) by means of the administration of a mycotoxin produced by *Aspergillus ochraceus* which is present as a contaminant in various foodstuffs and is known as ochratoxin A (Kniper-Goodman T., Scott P., Biomed. Environ. Sci., 2, 179, 1989).

The administration of small amounts of this toxin causes a series of renal abnormalities in the rat with a reduction in glomerular filtration and lesions at the level of the proximal tubule to such an extent as to cause renal atrophy. With a panel of tests conducted in rats intoxicated with ochratoxin A, it proved possible to demonstrate that, in this experimental model, too, the administration of the combination of acetyl L-carnitine and propionyl L-carnitine exerts an important protective effect against the renal abnormalities induced by the toxin. This effect is surprisingly greater than would be expected on summing the single effects obtained with the use of acetyl L-carnitine alone or propionyl L-carnitine alone.

In this test a batch of Wistar rats with a mean body weight of 200 g was divided into various groups, one of which served as a control group, while another was administered 300 mg/kg of ochratoxin (Sigma Chemical, St. Louis, Mo. U.S.A.) by gastric probe every 48 hours for a period of ten days. The remaining groups, in addition to ochratoxin, also received oral administrations of 300 mg/ks of acetyl L-carnitine or 300 mg/kg of propionyl L-carnitine or a combination of the two carnitines for the entire 10-day treatment period.

At the end of treatment, the animals were placed in metabolic cages and 24-hour urine was submitted to spectrophotometric evaluation of the enzymes alkaline phosphatase (ALP), gamma-glutamyl transferase (GGT) and N-acetyl-β-D-glucosaminidase (NAG) as indicators of renal damage.

Serum creatinine concentrations were also measured.

On the basis of the results of these tests (see Table 2) the high degree of enzymuria induced by ochratoxin and serum creatinine levels are shown to be reduced by the administration both of acetyl L-carnitine and propionyl L-carnitine alone. However, a surprisingly greater protective effect was achieved with the administration of the combination of acetyl L-carnitine plus propionyl L-carnitine, thus demonstrating the potent synergistic effect produced by the combination.

TABLE 2

Protective activity against renal abnormalities induced by ochratoxin A

| Ochratoxin | Treatm. | mg/kg | ALP (U/I) | GGT (U/I) | NAG (U/I) | Serum creatinine (mg/100 ml) |
|---|---|---|---|---|---|---|
| Cotrols | | | 3.5 ± 0.8 | 11.6 ± 1.7 | 31.1 ± 3.3 | 250.6 ± 19.2 |
| Ochratoxin A | | | 9.6 ± 1.4 | 18.9 ± 2.1 | 50.2 ± 4.6 | 620.4 ± 45.5 |
| | ACL | 300 | 8.8 ± 1.1 | 17.2 ± 1.9 | 48.8 ± 5.1 | 570.2 ± 50.4 |
| | PC | 300 | 7.5 ± 0.9 | 16.5 ± 2.2 | 44.2 ± 4.5 | 505.9 ± 46.4 |
| | ACL + PC | 300 | 4.8 ± 1.2 | 13.3 ± 1.9 | 36.8 ± 3.9 | 390.5 ± 30.6 |

ACL = Acetyl L-carnitine
PC = Propionyl L-carnitine

Protective Activity Against Lithium-Induced Nephrotoxicity in the Isolated Perfused Kidney This test was used to assess the protective activity of the combination of acetyl L-carnitine plus propionyl L-carnitine against the well-known nephrotoxic activity of lithium. Lithium presents a particular tropism at the renal tubule level and can cause tubular necrosis.

In this test Wistar rates with a mean body weight of 400 g were anaesthetised and nephrectomised. The excised kidneys were perfused according to the technique described by Shureck (Shureck H. J., Pflügers Arch., 354, 1975) as modified by Maach (Maach T., Kidney Int., 30, 142, 1986; Maach T., Ann. J. Physiol., 238, 1980).

Immediately after isolation of the kidney, the renal artery and outflow vein were catheterised and the resulting preparation was placed in a chamber containing a Krebs solution heated to 37° C. The oxygenised Krebs solution was pumped into the system by means of a pulsatile pump at a rate of 0.8 ml/min/g.

Lithium was administered via the perfusion pump at a dose of 6 mEq/L after perfusion during the previous 20 minutes of a solution containing acetyl L-carnitine or propionyl L-carnitine (200 mM/L) or a combination of the two compounds.

After the lithium infusion, the venous perfusion fluid was collected at five-minute intervals for fifteen minutes and its histamine content was measured with a fluorometric method (Hakanson R., Anal. Biochem., 47, 356, 1972). Histamine release is considered a marker of the severity of tubular damage (Bertelli A., Drugs Exptl. Clin Res., 7, 53, 1981).

As shown by the data reported in Table 3, the histamine release induced by the renal toxic action of lithium was reduced by the perfusion of acetyl L-carnitine or propionyl L-carnitine, but the greatest reduction was brought about by administration of the two carnitines in combination. The results of this test also demonstrate the potent synergistic kidney-protecting effect exerted by the combination of acetyl L-carnitine plus propionyl L-carnitine.

TABLE 3

Percentage changes vs controls in histamine released in the isolated kidney by lithium alone and after infusion of acetyl L-carnitine or propioNyl L-carnitine or a combination of acetyl L-carnitine plus propionyl L-carnitine

| | Post-lithium-infusion time (in minutes) | | |
|---|---|---|---|
| | 5 | 10 | 15 |
| Lithium | 65 ± 5.9 | 42.2 ± 3.6 | 15.1 ± 1.9 |
| ACL + lithium | 55.8 ± 6.1 | 36.8 ± 3.1 | 12.5 ± 1.5 |
| PC + lithium | 45.8 ± 4.5 | 30.4 ± 2.9 | 10.4 ± 0.9 |
| ACL + PC + lithium | 21.4 ± 2.5 | 16.2 ± 0.2 | 5.5 ± 0.3 |

ACL = Acetyl L-carnitine
PC = Propionyl L-carnitine

Some non-limiting examples of compositions according to the invention are given hereinbelow.

| | | | |
|---|---|---|---|
| 1) | Acetyl L-carnitine | 1000 | mg |
| | Propionyl L-carnitine | 1000 | mg |
| 2) | Acetyl L-carnitine | 500 | mg |
| | Propionyl L-carnitine | 500 | mg |
| 3) | Acetyl L-carnitine | 250 | mg |
| | Propionyl L-carnitine | 250 | mg |
| 4) | Acetyl L-carnitine | 200 | mg |
| | Propionyl L-carnitine | 200 | mg |
| | L-carnitine | 200 | mg |
| | ValeryL L-carnitine | 200 | mg |
| | Butyryl L-carnitine | 200 | mg |
| 5) | Acetyl L-carnitine | 200 | mg |
| | Propionyl L-carnitine | 200 | mg |
| | L-carnitine | 100 | mg |
| | Coenzyme $Q_{10}$ | 25 | mg |
| | Vitamin E | 5 | mg |
| | Vitamin C | 100 | mg |
| | Linoleic acid | 50 | mg |
| | Linolenic acid | 50 | mg |
| | L-cysteine | 50 | mg |
| | N-acetylcysteine | 50 | mg |
| 6) | Acetyl L-carnitine | 200 | mg |
| | Propionyl L-carnitine | 200 | mg |
| | L-carnitine | 200 | mg |
| | Coenzyme $Q_{10}$ | 20 | mg |
| | Resveratrol | 1 | mg |
| | Vitamin E | 5 | mg |
| | Vitamin C | 100 | mg |
| | β-carotene | 2 | mg |
| | Lycopene | 5 | mg |
| | Riboflavin | 10 | mg |
| | Pyridoxine | 10 | mg |
| | Pantothenic acid | 50 | mg |

What is meant by pharmacologically acceptable salt of L-carnitine or alkanoyl L-carnitine is any salt of these with an acid that does not give rise to unwanted toxic or side effects. Such acids are well known to pharmacologists and to experts in pharmaceutical technology.

Examples of such acids, though not exclusively these, are: chloride; bromide; iodide; aspartate, acid aspartate; citrate, acid citrate; tartrate; phosphate, acid phosphate; fumarate, acid fumarate; glycerol phosphate; glucose phosphate; lactate; maleate, acid maleate; orotate; oxalate, acid oxalate; sulphate, acid sulphate; trichloroacetate; trifluoroacetate and methane sulphonate.

A list of FDA-approved pharmacologically acceptable salts is given in *Int. J. of Pharm.* 33, 1986, 201-217. This publication is incorporated herein by reference.

The compositions of the invention can be formulated as tablets, lozenges, pills, capsules, granulates, syrups, vials or drops.

The invention claimed is:

1. A method for providing kidney protection from a kidney dysfunction caused by lithium which comprises administering to an individual in need thereof a therapeutically effective amount of acetyl L-carnitine and propionyl L-carnitine or a pharmacologically acceptable salt thereof, in which the weight-ratio of acetyl L-carnitine to propionyl L-carnitine is 1:1.

2. A method for providing protection from a kidney dysfunction caused by lithium which comprises administering to an individual in need thereof a combination composition of a therapeutically effective amount of acetyl L-carnitine and propionyl L-carnitine or a pharmacologically acceptable salt thereof, in which the weight-ratio of acetyl L-carnitine to propionyl L-carnitine is 1:1.

3. A method for providing protection from nephropathy caused by lithium which comprises administering to an individual in need thereof a combination composition of a therapeutically effective amount of acetyl L-carnitine and propionyl L-carnitine or a pharmacologically acceptable salt thereof, in which the weight-ratio of acetyl L-carnitine to propionyl L-carnitine is 1:1.

4. A method for providing protection from tubular necrosis caused by lithium which comprises administering to an individual in need thereof a therapeutically effective amount of a combination composition of a therapeutically effective amount of acetyl L-carnitine and propionyl L-carnitine or a pharmacologically acceptable salt thereof, in which the weight-ratio of acetyl L-carnitine to propionyl L-carnitine is 1:1.

5. A method for providing protection from tubular necrosis caused by lithium which comprises administering to an individual in need thereof a therapeutically effective amount of acetyl L-carnitine and propionyl L-carnitine or a pharmacologically acceptable salt thereof, in which the weight-ratio of acetyl L-carnitine to propionyl L-carnitine is 1:1.

6. A method for providing protection from tubular necrosis caused by lithium which comprises administering to an individual in need thereof 2-5 mg/kg body weight/day of acetyl L-carnitine and 2-5 mg/kg body weight/day of propionyl L-carnitine or an equimolar amount of a pharmacologically acceptable salt thereof, in which the weight-ratio of acetyl L-carnitine to propionyl L-carnitine is 1:1.

7. A method for providing protection from a kidney dysfunction caused by lithium which comprises administering to an individual in need thereof a combination composition of 2-5 mg/kg body weight/day of acetyl L-carnitine and 2-5 mg/kg body weight/day of propionyl L-carnitine or an equimolar amount of a pharmacologically acceptable salt thereof, in which the weight-ratio of acetyl L-carnitine to propionyl L-carnitine is 1:1.

8. A method for providing protection from nephropathy caused by lithium which comprises administering to an individual in need thereof a combination composition of 2-5 mg/kg body weight/day of acetyl L-carnitine and 2-5 mg/kg body weight/day of propionyl L-carnitine or an equimolar amount of a pharmacologically acceptable salt thereof, in which the weight-ratio of acetyl L-carnitine to propionyl L-carnitine is 1:1.

9. A method for providing protection from tubular necrosis caused by lithium which comprises administering to an individual in need thereof a therapeutically effective amount of a combination composition of 2-5 mg/kg body weight/day of acetyl L-carnitine and 2-5 mg/kg body weight/day of propionyl L-carnitine or an equimolar amount of a pharmacologically acceptable salt thereof, in which the weight-ratio of acetyl L-carnitine to propionyl L-carnitine is 1:1.

* * * * *